(12) United States Patent
Beverland et al.

(10) Patent No.: US 11,602,285 B2
(45) Date of Patent: Mar. 14, 2023

(54) PELVIC REFERENCING GUIDE

(71) Applicant: DEPUY IRELAND UNLIMITED COMPANY, County Cork (IE)

(72) Inventors: David Beverland, N. Ireland (GB); Sarah Bushell, Sheffield (GB); Conor Lowry, Leeds (GB); Stephanie Prince, Wakefield (GB); Philippa Withers, London (GB); Duncan Young, Melbourn (GB)

(73) Assignee: DEPUY IRELAND UNLIMITED COMPANY

( * ) Notice: Subject to any disclaimer, the term of this patent is extended or adjusted under 35 U.S.C. 154(b) by 940 days.

(21) Appl. No.: 16/469,532

(22) PCT Filed: Dec. 8, 2017

(86) PCT No.: PCT/EP2017/081976
§ 371 (c)(1),
(2) Date: Jun. 13, 2019

(87) PCT Pub. No.: WO2018/108729
PCT Pub. Date: Jun. 21, 2018

(65) Prior Publication Data
US 2019/0313945 A1 Oct. 17, 2019

(30) Foreign Application Priority Data
Dec. 15, 2016 (GB) .................... 1621373

(51) Int. Cl.
*A61B 5/107* (2006.01)
*A61B 5/00* (2006.01)
*A61B 90/00* (2016.01)
*G01B 5/24* (2006.01)

(52) U.S. Cl.
CPC .......... *A61B 5/1071* (2013.01); *A61B 5/4504* (2013.01); *A61B 5/4571* (2013.01); *A61B 2090/068* (2016.02); *G01B 5/24* (2013.01)

(58) Field of Classification Search
None
See application file for complete search history.

(56) References Cited

U.S. PATENT DOCUMENTS

| | | | | |
|---|---|---|---|---|
| 4,846,194 A | * | 7/1989 | Sabia | A61B 5/107 33/512 |
| 5,966,827 A | * | 10/1999 | Horvath | A61B 5/103 33/512 |
| 6,421,928 B1 | * | 7/2002 | Miller | A47G 1/205 33/669 |
| 6,871,413 B1 | | 3/2005 | Arms | |
| 8,739,423 B1 | * | 6/2014 | Cortum | G01C 9/28 33/613 |

(Continued)

FOREIGN PATENT DOCUMENTS

| | | |
|---|---|---|
| CN | 103491893 A | 1/2014 |
| CN | 104220021 A | 12/2014 |

(Continued)

*Primary Examiner* — Christopher W Fulton

(57) ABSTRACT

The present invention relates generally to the field of orthopedics, and more particularly to a pelvic referencing guide and methods of using the guide in orthopaedic surgery, specifically total hip arthroplasty.

14 Claims, 4 Drawing Sheets

(56) References Cited

U.S. PATENT DOCUMENTS

Figure 1:
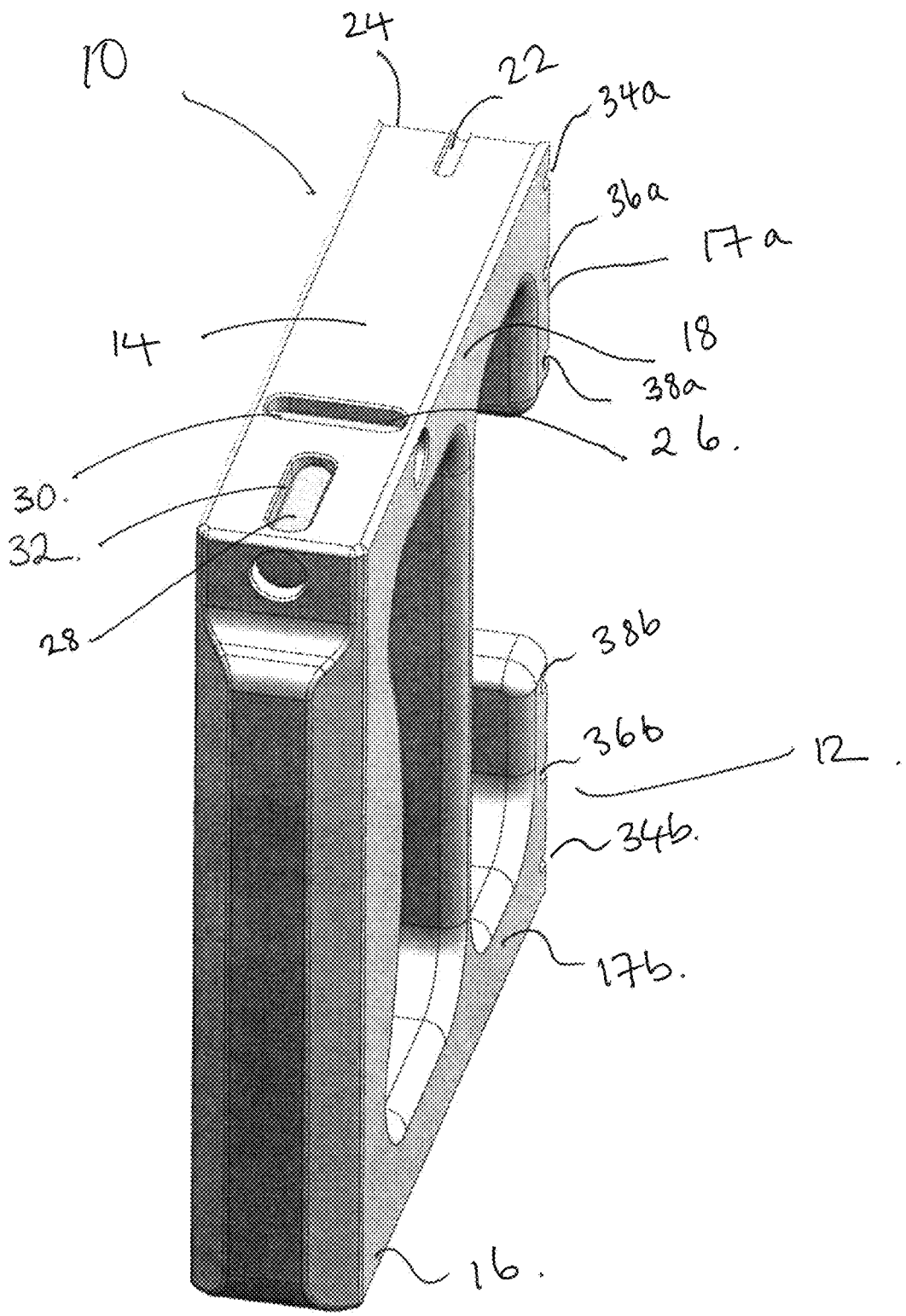

| | | | | |
|---|---|---|---|---|
| 9,032,637 | B2 * | 5/2015 | Propp | B25H 7/04 |
| | | | | 33/669 |
| 9,662,228 | B2 * | 5/2017 | McCarthy | A61B 34/10 |
| 2007/0021644 | A1 | 1/2007 | Woolson | |
| 2009/0188121 | A1 * | 7/2009 | Rabin | G01C 9/26 |
| | | | | 33/332 |
| 2012/0203140 | A1 | 8/2012 | Malchau | |
| 2013/0269196 | A1 | 10/2013 | Steele | |
| 2014/0190030 | A1 | 7/2014 | Sano | |
| 2015/0245914 | A1 | 9/2015 | Langton | |
| 2016/0146603 | A1 * | 5/2016 | Lamont | G01C 9/34 |
| | | | | 33/381 |
| 2016/0302727 | A1 | 10/2016 | Aghazadeh | |
| 2016/0345868 | A1 * | 12/2016 | Rost | A61B 5/1071 |

FOREIGN PATENT DOCUMENTS

| | | | | |
|---|---|---|---|---|
| DE | 202007014519 U1 | 2/2008 | | |
| EP | 812661 A2 * | 12/1997 | | B25H 7/00 |
| KR | 2016047749 A | 5/2016 | | |
| TW | M369135 U | 11/2009 | | |
| WO | WO-03030729 A2 * | 4/2003 | | A61B 5/1071 |

* cited by examiner

STEP 1

STEP 2

STEP 3

STEP 4

STEP 5a

STEP 5b

PELVIC REFERENCING GUIDE

CROSS REFERENCE TO RELATED PCT APPLICATION

This application is a National Stage 35 U.S.C. 371 of International Patent Application PCT/EP2017/081976 filed Dec. 8, 2017, which claims priority to United Kingdom Application No. GB 1621373.8, filed Dec. 15, 2016, both of which are incorporated by reference in their entireties.

FIELD OF THE INVENTION

The present invention relates generally to the field of orthopedics, and more particularly to a pelvic referencing guide and methods of using the guide in orthopedic surgery, specifically total hip arthroplasty.

BACKGROUND OF THE INVENTION

The majority of post-operative adverse events, such as dislocation, impingement and increased wear following total hip arthroplasty may be attributed to malposition of the implanted acetabular component. The orientation (inclination/anteversion) of the acetabular component is influenced not only by the orientation at which the surgeon implants the component, but also the orientation of the pelvis at the time of implantation. Hence, the orientation of the pelvis at set up and its movement during the operation are important factors.

Mechanical acetabular cup positioning guides are not traditionally connected to the position of the pelvis. Indeed, they assume perfect pelvic orientation. However in reality, due to patient anatomy (i.e., shoulders being smaller/larger than hips) the pelvis will tend to tilt either towards the feet or the head. If the pelvis is tilted towards the feet, the cup inclination angle will increase. If the pelvis is tilted towards the head the cup inclination angle will decrease. Pelvic tilt will also have an effect on the anteversion angle of an implanted acetabular cup.

In addition, due to the fact that there is normally more bulk at the front of the patient than at the back, the pelvis tends to internally rotate. If the pelvis is internally rotated, the cup anteversion angle will reduce. If the pelvis is externally rotated, the cup anteversion angle will increase. Pelvic rotation will also have an effect on the inclination angle of an implanted acetabular cup.

In order to enhance the accuracy of the placement of the acetabular component when using a direct lateral approach, a posterior lateral approach, a posterior approach or an anterior lateral approach, the surgeon will want the patient to be placed in a position in which the pelvis correctly aligned and restrained.

Conventionally, a surgeon visually undertakes pelvic alignment in order to minimise the anterior or posterior tilt of the pelvis during the implantation of the acetabular component.

There is provided a pelvic referencing guide and methods of using the guide for positioning a patient in the lateral decubitus position, at least prior to surgery, such that the pelvis is correctly aligned for the implantation of the acetabular component, thereby minimising the post-operative adverse events. This guide utilises anatomical reference points, such as the left posterior superior iliac spine and the right posterior superior iliac spine, commonly referred to as the PSIS points, in order to measure and correct (if necessary) the pelvic tilt.

SUMMARY OF THE INVENTION

According to an aspect of the invention there is provided a pelvic referencing guide for use in determining the orientation of a patient's pelvis when the patient is placed in a lateral decubitus position, the guide comprising a body portion having a planar patient facing surface, a reference mark for aligning with a transverse pelvic line on the patient's skin which extends between an underlying right posterior superior iliac spine and left posterior superior iliac spine, and an inclinometer for indicating the orientation of the transverse pelvic line in at least one vertical plane.

In some embodiments, the body portion includes a first transverse surface that extends transverse to the patient facing surface, with the reference mark being provided on this first transverse surface. The reference mark can extend inwardly from an edge of the first transverse surface that adjoins the planar patient facing surface. The reference mark is positioned centrally along this edge. The reference mark can be a groove formed within the surface of the first transverse surface. In other constructions, the reference mark can be a line that is etched into or applied onto the surface of the first transverse surface.

It is particularly advantageous that the device includes at least two reference marks that can be simultaneously aligned with the transverse pelvic line. This improves the accuracy of the measurement by the inclinometer. The body portion can include a second transverse surface that extends transverse to the patient facing surface and parallel with the first transverse surface, the second transverse surface including a second reference mark which is aligned with the reference mark on the first transverse surface such that the reference marks on the first and second transverse surfaces can be simultaneously aligned with the transverse pelvic line.

For ease of use, it is preferable if the use of the guide is not orientation specific. To achieve this the inclinometer can be provided on the first transverse surface, the second transverse surface or both. The inclinometer can be in the form of a spirit level. The spirit level can be embedded within the first transverse surface and/or the second transverse surface. In other constructions, the inclinometer is a digital inclinometer. In some constructions the inclinometer is temporarily or permanently secured to the first transverse surface and/or the second transverse surface.

In some constructions, an inclinometer is provided which allows the orientation of the transverse pelvic line to be assessed within the transverse plane.

In some constructions, an inclinometer is provided which allows the orientation of the transverse pelvic line to be assessed within the coronal plane.

In some constructions, an inclinometer is provided which allows the orientation of the transverse pelvic line to be assessed within both the transverse plane and the coronal plane.

The distance between the PSIS points on patients can vary. Indicia can therefore be provided on the guide in order to help the surgeon to centre the guide relative to the patient's PSIS points. This improves the accuracy of the inclinometer feedback. For example, the guide can further comprise a side surface extending at least partly between the first transverse surface and the second transverse surface, the side surface being provided with a pair of indicia comprising a first indicium for placing over the right posterior superior iliac spine and a second indicium for placing over the left posterior superior iliac spine such that the guide can be centred on the patient. Examples of suitable forms of indicia are known to the person skilled in the art, and include, but are not limited to, the provision of a groove or a rib on the side surface, or a laser or etch marking provided on the side surface.

In some constructions, the guide is configured such that the first indicium is moveable with respect to the second indicium. The ability of the surgeon to be able to adjust the spacing of the indicium with respect to each other allows the guide to accommodate differing spacing between the right posterior superior iliac spine and the left posterior superior iliac spine of different patients.

In other constructions in which the first indicium is not moveable with respect to the second indicium the side surface is provided with at least a second pair of indicia comprising a first indicium for placing over the right posterior superior iliac spine and a second indicium for placing over the left posterior superior iliac spine.

As mentioned above, for ease of use, it is preferable if the use of the guide is not orientation specific. To achieve this the guide can include a second side surface extending at least partly between the first transverse surface and the second transverse surface. This second side surface can include at least a first pair of indicia comprising a first indicium for placing over the right posterior superior iliac spine and a second indicium for placing over the left posterior superior iliac spine. The location of the indicia on the second side surface can be the same or different to the location of the indicia on the first side surface.

To further aid in the use of the guide, an ergonomic handle is provided. The handle may be attached to a part of the guide or formed as an integral part of the guide.

In some constructions, the guide can be sterilised.

According to a second aspect of the invention there is provided a method of determining the orientation of a patient's pelvis when the patient is in a lateral decubitus position, the method comprising the steps of;
(a) providing a pelvic referencing guide comprising:
 a body portion having a planar patient facing surface,
 a reference mark for aligning with a transverse pelvic line on the patient's skin which extends between an underlying right posterior superior iliac spine and left posterior superior iliac spine, and
 an inclinometer for indicating the orientation of the transverse pelvic line in at least one vertical plane;
(b) positioning the guide relative to the transverse pelvic line such that the reference mark is aligned with a part of the transverse pelvic line;
(c) assessing using the inclinometer the orientation of the transverse pelvic line in at least one vertical plane.

According to a further aspect of the invention there is provided a method for guiding an operator in altering an orientation of a pelvis of a patient for subsequent insertion of a pelvic implant, comprising the steps of:
(a) placing a patient in a lateral decubitus position;
(b) using a pelvic referencing guide comprising
 a body portion having a planar patient facing surface,
 a reference mark for aligning with a transverse pelvic line on the patient's skin, the line extending between an underlying right posterior superior iliac spine and left posterior superior iliac spine, and
 an inclinometer for indicating the orientation of the transverse pelvic line in at least one vertical plane;
(c) positioning the planar patient facing surface of the guide against the patient's skin such that the reference mark is aligned with a part of the transverse pelvic line;
(d) assessing using the inclinometer the orientation of the transverse pelvic line in at least one vertical plane, and optionally
(e) repositioning the patient to a position in which the orientation of the transverse pelvic line is vertical in the at least one vertical plane.

The operating table can be tilted in order to adjust the patient's pelvic position, or the patient can be repositioned to adjust the orientation of the previously marked transverse pelvic line within the at least one vertical plane. The vertical plane is the transverse plane and/or the coronal plane.

It is envisaged that the guide can be used to position a patient pre-operatively.

It is also envisaged that the guide might be used within the sterile field intra-operatively to ensure that the required pelvic tilt is maintained. However, conventional patient restraints used during hip surgery, such as clamps, may obscure the PSIS points intra-operatively. Therefore, if the pelvic referencing guide of the present invention is to be used to intra-operatively, the patient restraints might require modification in order to allow visualisation of the PSIS points. It is also envisaged that a patient might be clamped in a manner that will allow access to the PSIS points intra-operatively.

Furthermore, the surgical drapes covering the patient might be provided with windows to allow the intra-operative visualisation of the PSIS points.

DETAILED DESCRIPTION OF THE INVENTION

Figure 2:
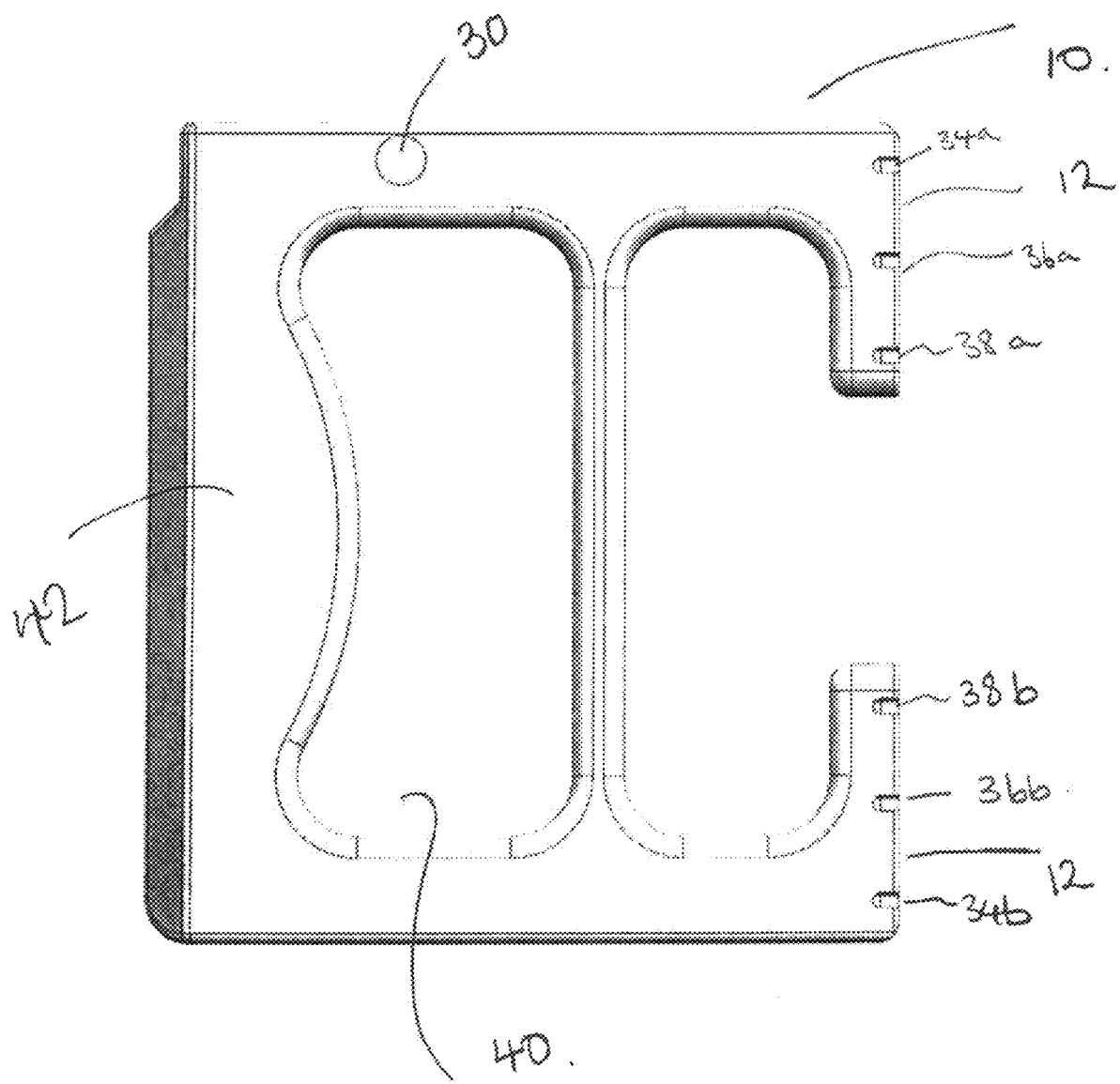
Figure 3:
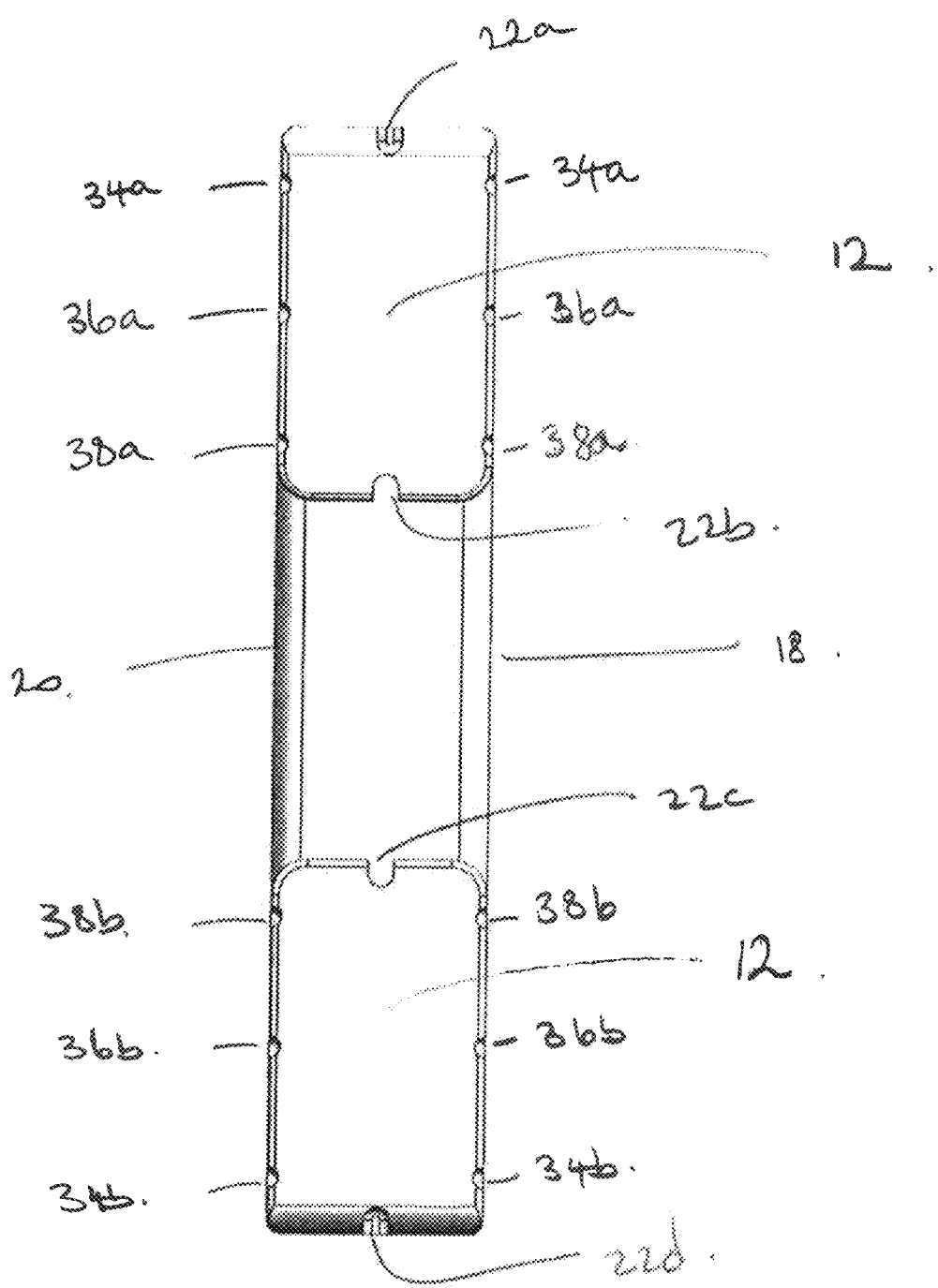

The invention will now be described, by way of example only, with reference to the following drawings, in which:

FIG. 1: Shows a rear view of a construction of the pelvic referencing guide;

FIG. 2: Shows a side view of the pelvic referencing guide of FIG. 1;

FIG. 3: Shows a front view of the pelvic referencing guide of FIG. 1.

Figure 4:
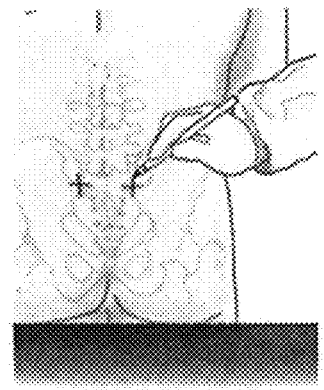
Figure 4:
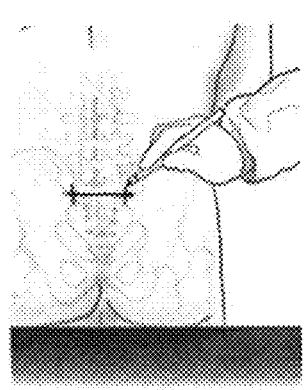
Figure 4:
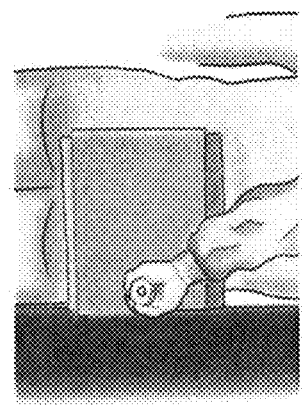
Figure 4:
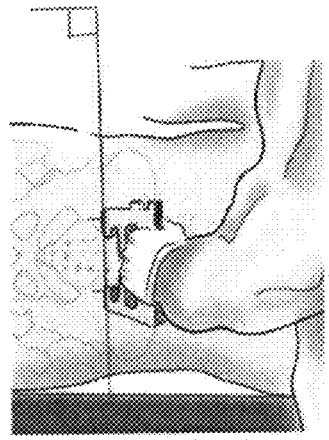
Figure 4:
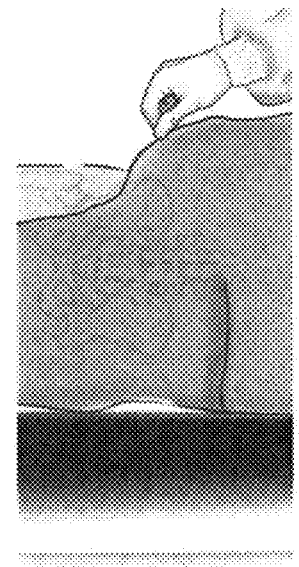
Figure 4:
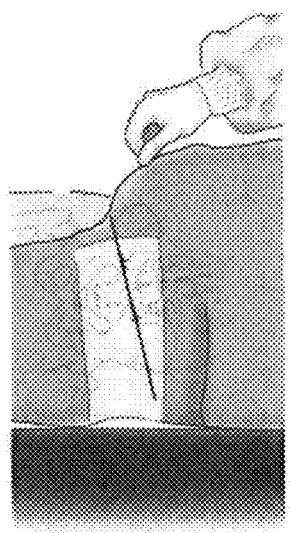

FIG. 4: Shows a method of using the pelvic referencing guide of FIG. 1 to align a patient's pelvis.

FIG. 1 shows a construction of the pelvic referencing guide 10 which includes a planar patient facing surface 12, a first transverse surface 14 that extends from a top edge of the patient facing surface and transverse thereto, a second transverse surface 16 that extends from a bottom edge of the patient facing surface 12, and is substantially parallel to the first transverse surface 14, and first and second 18, 20 side surfaces that extend between the first transverse surface 14 and the second transverse surface 16. The planar patient facing surface is formed by two spaced apart feet 17a, 17b. First foot 17a can be in a fixed position relative to second foot 17b. Optionally, the feet can be configured such that at least one of first foot 17a and second foot 17b can be moved towards and away from the other foot in order to reduce or increase the gap between them. In some constructions, both feet are configured to be movable.

A reference mark, in the form of a groove 22, is provided on the first transverse surface 14. The groove in this construction of the guide extends inwardly from an edge 24 of the first transverse surface 14 that adjoins the top edge of the planar patient facing surface 12. The groove is positioned centrally along this edge. As shown in FIG. 3, the guide includes four aligned reference marks (22a-22d) associated with the planar patient facing surface. These reference marks can be simultaneously aligned with the transverse pelvic line.

The first transverse surface 14 is also provided with two inclinometers in the form of spirit levels. The first inclinometer 26 is used to indicate the position of the transverse pelvic line in a first vertical plane. The first vertical plane is the coronal plane. The second inclinometer 28 is used to indicate the position of the transverse pelvic line in a second vertical plane. The second vertical plane is the sagittal plane. In this construction of the guide, both inclinometers are embedded within channels 30, 32, such that the top of each inclinometer is flush or subflush with the planar patient facing surface.

The second transverse surface 16 can also be provided with first and second inclinometers 26, 28 in the same manner as described for the first transverse surface.

The guide shown in this construction includes three pairs of indicia (34, 36, 38) on both the first side surface 18 and second side surface 20. The pairs of indicia are spaced in order to help the surgeon to centre the device on the patient. This is useful because of the variability in the spacing of the PSIS points between patients. Each pair of indicia comprises a first indicium 34a, 36a, 38a provided on the first foot 17a for placing over the right posterior superior iliac spine and a second indicium 34b, 36b, 38b provided on the second foot 17b for placing over the left posterior superior iliac spine. The spacing between the indicium 36a, 36b in the second pair of indicia 36 is less than the spacing between the indicium 34a, 34b in the first pair of indicia 34. The spacing between the indicium 38a, 38b in the third pair of indicia 38 is less than the spacing between the indicium 36a, 36b in the second pair of indicia 34.

An investigation into the variability between the distance between PSIS points in a patient group showed that the smallest gap between PSIS point is about 49.7 mm and the largest gap between PSIS point is about 117.9 mm. A gap of about 50 mm between the edges of the feet was therefore selected as this enables the guide to be centred on the smallest PSIS gap, whilst also allowing the feet to accommodate the variations in distance seen between patients. The distance between the indicium 34a and 34b is about 140 mm.

In order to centre the device on the patient, when the guide is positioned with the right PSIS point located between 34a and 36a, the left PSIS point should fall between 34b and 36b. If this is not the case, the device should be moved up or down along the transverse pelvic line to ensure that both PSIS marks are aligning relatively with the same indicia on each foot.

It is however envisaged that the device may include a single pair of indicia, with one of the pair being provided on first foot 17a and the other indicium of the pair being provided on second foot 17b. For example, first indicium 34a may be provided on first foot 17a and second indicium 34b may be provided on second foot 17b. For example, first indicium 36a may be provided on first foot 17a and second indicium 36b may be provided on second foot 17b. For example, first indicium 38a may be provided on first foot 17a and second indicium 38b may be provided on second foot 17b.

FIG. 2 shows a side view of the device. A cut-out section 40 within the device is sized for receipt of at least some of the surgeon's fingers. This allows the surgeon to grasp the device around a handle 42.

FIG. 3 shows a front view of the device. The planar patient facing surface 12 is divided into a first foot portion 17a and a second foot portion 17b.

FIG. 4 shows a method of using the pelvic referencing guide to position a patients' pelvis.

Step 1: Position patient upright (e.g., on the central portion of the operating table with feet over the side and supported on a stool) and mark out the left and right PSIS points;

Step 2: Mark a horizontal line (i.e., the transverse pelvic line), that transects the PSIS points;

Step 3: Position the patient in a lateral decubitus position and secure with patient restraints;

Step 4: Use the pelvic referencing guide to fine tune the position of the pelvis by adjusting the patient restraints (e.g., front and back props) to ensure that there is zero internal/external pelvic rotation. Use the indicia on the side surface to centre the device on the patient. Use the reference mark on the first transverse surface and the second transverse surface to align the guide with the transverse pelvic line. Adjust the angle of the table to ensure that the transverse pelvic line is vertical.

Step 5: Position drapes over the patient. As shown in FIG. 5a, the use of a regular drape will conceal the pelvis. Any further movement of the pelvis will be invisible to the surgeon. As shown in FIG. 5b, the use of an alternative drape which ensures that the transverse pelvic line is remains visible during surgery allows the orientation of the pelvis to be checked or monitored throughout surgery.

The invention claimed is:

1. A method of determining the orientation of a patient's pelvis when the patient is in a lateral decubitus position, the method comprising the steps of:

(a) using a pelvic referencing guide comprising;
a body portion having a planar patient facing surface, a first transverse surface that extends away from and transverse to the patient facing surface and on which reference mark is provided, and a second transverse surface that extends away from and transverse to the patient facing surface and parallel with the first transverse surface, the second transverse surface including a second reference mark which is aligned with the reference mark on the first transverse surface such that the reference marks on the first and second transverse surfaces can be simultaneously aligned with the transverse pelvic line on the patient's skin, the line extending between an underlying right posterior superior iliac spine and left posterior superior iliac spine, and an inclinometer for indicating the orientation of the transverse pelvic line in at least one vertical plane;

(b) positioning the planar patient facing surface of the guide against the patient's skin such that the reference mark is aligned with a part of the transverse pelvic line; and (c) assessing using the inclinometer the orientation of the transverse pelvic line in at least one vertical plane.

2. The method of claim 1, wherein the at least one vertical plane is a transverse plane or a coronal plane.

3. A pelvic referencing guide for use in determining the orientation of a patient's pelvis when the patient is placed in a lateral decubitus position, the guide comprising a body portion having a planar patient facing surface, a reference mark for aligning with a transverse pelvic line on the patient's skin which extends between an underlying right posterior superior iliac spine and left posterior superior iliac spine, and an inclinometer for indicating the orientation of the transverse pelvic line in at least one vertical plane, wherein the body portion includes a first transverse surface that extends away from and transverse to the patient facing surface and on which the reference mark is provided, and a second transverse surface that extends away from and transverse to the patient facing surface and parallel with the first transverse surface, the second transverse surface including a second reference mark which is aligned with the reference mark on the first transverse surface such that the reference marks on the first and second transverse surfaces can be simultaneously aligned with the transverse pelvic line.

4. The guide of claim 3, wherein the reference mark extends inwardly from an edge of the first transverse surface that adjoins the planar patient facing surface, the reference mark being positioned centrally along the edge.

5. The guide of claim 3, wherein the reference mark is a groove formed within the surface.

6. The guide of claim 3, wherein the inclinometer is provided on at least one of the first transverse surface and the second transverse surface.

7. The guide of claim 3, wherein the inclinometer is a spirit level or a digital inclinometer.

8. The guide of claim 3, wherein guide further comprises a side surface extending at least partly between the first transverse surface and the second transverse surface, the side surface being provided with a pair of indicia comprising a first indicium for placing over the right posterior superior iliac spine and a second indicium for placing over the left posterior superior iliac spine such that the guide can be centered on the patient.

9. The guide of claim 8, wherein guide is configured such that the first indicium is moveable with respect to the second indicium.

10. The guide of claim 8, wherein the side surface is provided with at least a second pair of indicia comprising a first indicium for placing over the right posterior superior iliac spine and a second indicium for placing over the left posterior superior iliac spine.

11. The guide of claim 3, wherein the guide comprises a second side surface extending at least partly between the first transverse surface and the second transverse surface.

12. The guide of claim 11, wherein the second side surface further comprises a pair of indicia comprising a first indicium for placing over the right posterior superior iliac spine and a second indicium for placing over the left posterior superior iliac spine such that the guide can be centered on the patient.

13. The guide of claim3, wherein the guide includes a handle.

14. The guide of claim 3, wherein the at least one vertical plane is a transverse plane or a coronal plane.

* * * * *